(12) United States Patent
Schmidt (10) Patent No.: US 12,279,854 B2
(45) Date of Patent: Apr. 22, 2025

(54) PULSE SENSOR FOR DETECTING THE PULSE OF A LIVING ORGANISM

(71) Applicant: OSRAM Opto Semiconductors GmbH, Regensburg (DE)

(72) Inventor: Tobias Schmidt, Garching (DE)

(73) Assignee: OSRAM Opto Semiconductors GmbH, Regensburg (DE)

( * ) Notice: Subject to any disclaimer, the term of this patent is extended or adjusted under 35 U.S.C. 154(b) by 990 days.

(21) Appl. No.: 17/311,524

(22) PCT Filed: Dec. 13, 2019

(86) PCT No.: PCT/EP2019/085051
§ 371 (c)(1),
(2) Date: Jun. 7, 2021

(87) PCT Pub. No.: WO2020/126891
PCT Pub. Date: Jun. 25, 2020

(65) Prior Publication Data
US 2022/0015656 A1    Jan. 20, 2022

(30) Foreign Application Priority Data

Dec. 17, 2018 (DE) .......................... 102018221854.4

(51) Int. Cl.
*A61B 5/024* (2006.01)
*A61B 5/00* (2006.01)
*G06V 40/13* (2022.01)

(52) U.S. Cl.
CPC ........ *A61B 5/02427* (2013.01); *A61B 5/0071* (2013.01); *G06V 40/1318* (2022.01)

(58) Field of Classification Search
CPC .............. A61B 5/02427; A61B 5/0071; A61B 2562/0233; A61B 5/14552; G06V 40/1318
See application file for complete search history.

(56) References Cited

U.S. PATENT DOCUMENTS

2014/0275857 A1    9/2014 Toth et al.

FOREIGN PATENT DOCUMENTS

WO    WO-2018083351 A1 *   5/2018   ........... A61B 5/0059

\* cited by examiner

*Primary Examiner* — Keith M Raymond
*Assistant Examiner* — Patrick M Mehl
(74) *Attorney, Agent, or Firm* — Slater Matsil, LLP (57) ABSTRACT

In an embodiment a pulse sensor includes two light sources configured to emit light in a direction of a perfused tissue of a living being so that the perfused tissue scatters the light and so that the scattered light is modulated on basis of a pulse of the living being, at least one luminescent concentrator including an entry face, an exit face smaller than the entry face, and a fluorescent material arranged in a light path between the entry face and the exit face, wherein the luminescent concentrator is configured to receive at least some of the modulated scattered light entering through the entry face, convert the entered light by the fluorescent material and emit the modulated converted light from the exit face, and one light detector configured to detect at least some of the modulated converted light emerging from the exit face, wherein, in plan view, the luminescent concentrator is strip-shaped and extends perpendicular to a connecting line between the two light sources, wherein side faces of the luminescent concentrator facing the light sources are concave, and wherein corresponding side faces extend at least partially around the light sources.

20 Claims, 4 Drawing Sheets

PULSE SENSOR FOR DETECTING THE PULSE OF A LIVING ORGANISM

This patent application is a national phase filing under section 371 of PCT/EP2019/085051, filed Dec. 13, 2019, which claims the priority of German patent application 10 2018 221 854.4, filed Dec. 17, 2018, each of which is incorporated herein by reference in its entirety.

TECHNICAL FIELD

The invention relates to a pulse sensor for detecting the pulse of a living being.

BACKGROUND

In recent years, pulse sensors, i.e., heart rate monitors, have become ever more popular. In particular, there has been an unbroken boom of so-called fitness trackers, which generally are a digital wristwatch with a built-in heart rate monitor.

In these pulse sensors, light that is generally produced by one or more LEDs is coupled into the tissue of a human via the skin surface, with the skin intended to be understood as part of the tissue within the meaning of this patent application. The light is scattered by the tissue and experiences a modulation which corresponds to the pulse of the corresponding person. The origin of this modulation has not been fully resolved to date, although it is assumed that the modulation is caused by a changing density of the tissue around a blood vessel on account of the heartbeat and/or the varying amount of blood within a certain tissue dependent on the heartbeat. At least some of the scattered and correspondingly modulated light is detected by means of a light detector and the pulse of the corresponding person is ascertained on the basis of the modulation of the light.

A problem with these pulse sensors is that only a small fraction of the produced light arrives at the light detector. The remainder of the light either does not enter the tissue at all or is not scattered in the direction of the light detector by the tissue. Consequently, the ratio of detected light to produced light is low. This ratio is also expressed as efficiency of the pulse sensor. Consequently, the efficiency of conventional pulse sensors is low. The low efficiency leads to the signal produced by means of the light detector being relatively weak.

Moreover, most applications, for example wristwatches, require the corresponding pulse sensor to be particularly thin.

Figure 1:
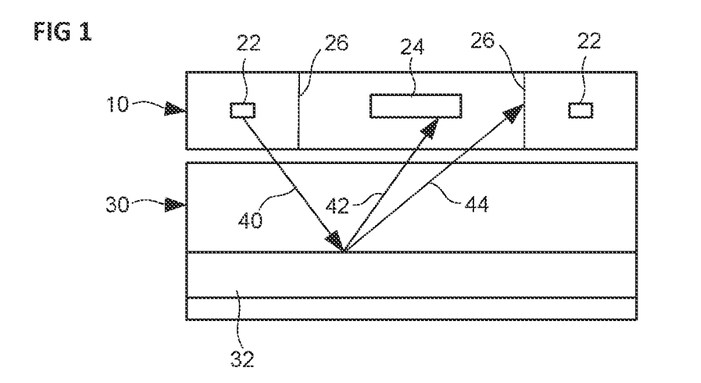
FIG. 1 shows a lateral sectional illustration of a conventional pulse sensor on a tissue of a living being.

FIG. 1 shows a conventional pulse sensor 10. The conventional pulse sensor 10 comprises at least one light source 22, two light sources 22 in the example shown, and at least one light detector 24. The light sources 22 and the light detector 24 are arranged in a housing of the conventional pulse sensor 10. Within the housing, the light sources 22 are separated from the light detector 24 by separating walls 26 so that none of the light produced by means of the light sources 22 can reach the light detector 24 directly. The housing and the separating walls 26 form three cavities, in which the two light sources 22 and the light detector 24 are arranged accordingly. The cavities can also be referred to as chambers. In FIG. 1, the cavities are open at the bottom such that the produced light can leave the pulse sensor 10 and the light to be detected can reach the light detector 24. The cavities are frequently filled with a transparent material, for example silicone.

The conventional pulse sensor 10 serves to detect a pulse of a living being. By way of example, the living being can be a human or an animal. The living being has a tissue 30, extending within which there is a blood vessel 32, for example a vessel, an artery, or a vein.

By way of example, the light produced by means of the light sources 22 can propagate along a first light path 40. The light propagating along the first light path 40 strikes the blood vessel 32, is scattered by the blood vessel 32, and experiences a modulation in the process, the latter being representative for the pulse of the living being. By way of example, the modulated scattered light can propagate along a second light path 42 and thus strikes the light detector 24, which detects the modulated scattered light. The light detector 24 produces an electric output signal that is representative for the detected light and its modulation and, in particular, is representative for the pulse of the living being. An evaluation unit (not illustrated) can receive and evaluate the output signal of the light detector 24. In particular, the evaluation unit can establish the pulse of the living being on the basis of the modulation of the light.

Only a small proportion of the light produced reaches the light detector 24 in the conventional pulse sensor 10. By way of example, the light scattered at the blood vessel 32 can propagate along a third light path 44 and thus strikes one of the separating walls 26 and not the light detector 24. Consequently, the efficiency of the conventional pulse sensor 10 is low.

SUMMARY

Embodiments provide a high-efficiency and/or thin pulse sensor for detecting the pulse of a living being.

Some embodiments provide a pulse sensor for detecting the pulse of a living being, comprising: at least one light source which is embodied and arranged in such a way that it emits light in the direction of a tissue perfused by blood of the living being when the pulse sensor is used as intended, wherein the perfused tissue scatters the light and wherein the scattered light is modulated on the basis of the pulse of the living being; at least one luminescent concentrator which comprises an entry face, an exit face that is smaller than the entry face, and fluorescent material arranged in the light path between the entry face and the exit face and which is embodied and arranged in such a way that at least some of the modulated scattered light enters into the luminescent concentrator through the entry face, that the light that has entered is converted by the fluorescent material, the converted light being modulated in a manner corresponding to the modulated scattered light, and that at least some of the modulated converted light propagates in the luminescent concentrator towards the exit face and emerges from the exit face; and at least one light detector which detects at least some of the modulated converted light emerging from the exit face.

The luminescent concentrator serves to collect light that was scattered in the tissue and guide said light to the light detector. Since the entry face of the luminescent concentrator is larger than the exit face of the luminescent concentrator, the luminescent concentrator causes a greater proportion of the scattered light to strike the light-sensitive area of the light detector than in the case without the concentrator. In descriptive terms, the luminescent concentrator collects a relatively large amount of light via its relatively large first entry face and guides said collected light to the comparatively relatively small light-sensitive area of the light detector. As a result, the efficiency of the heart rate monitor is high in comparison with a conventional heart rate monitor.

The above-described effects would also already exist if the concentrator were merely a passive optical concentrator. Passive optical concentrators only collect and transmit the light, but do not convert the light. Such passive optical concentrators only increase the irradiance or the illuminance and are subject to the physical constraint that diffuse light can only be concentrated up to the square of the refractive index of the utilized material.

However, the present luminescent concentrator with the fluorescent material is an active optical concentrator, which initially collects the modulated scattered light, then converts the latter and then transmits the modulated converted light. Additionally, the radiance or the luminance is increased in such an active optical concentrator. As a result, the concentration and hence the efficiency of the heart rate monitor is particularly high.

Moreover, such an active optical concentrator can have a relatively thin embodiment such that the corresponding heart rate monitor can also have a particularly thin embodiment.

By way of example, the light source can be an LED. In addition to the one light source, the heart rate monitor can comprise one, two or more further light sources. The light detector is, e.g., a photodiode or comprises, e.g., a photodiode. In addition to the photodiode, the light detector can comprise one, two or more further photodiodes. Moreover, the heart rate monitor can comprise a housing, within which the light source and the light detector are arranged. Here, the light source and the light detector are arranged in the housing in such a way that the light produced by means of the light source does not reach the light detector directly, i.e., without striking the tissue. For this purpose, the light source and the light detector can each be arranged in a cavity or chamber of the housing, with one cavity being separated from the other cavity by an opaque separating wall.

By way of example, the exit face of the luminescent concentrator can have the same shape and/or the same size as a light-sensitive area of the light detector. The luminescent concentrator can be in optical contact with the light-sensitive area of the light detector. The luminescent concentrator being in optical contact with the light-sensitive area of the light detector means that the light scattered in the tissue can reach the light-sensitive area of the light detector via the luminescent concentrator and that there is no region with a refractive index of less than 1.3 between the luminescent concentrator and the light-sensitive area of the light detector. This means that the modulated converted light can reach the light-sensitive area of the light detector through the luminescent concentrator and possibly through an adhesive which is used to fasten the light detector against the luminescent concentrator.

The luminescent concentrator is formed in one piece according to one development. This contributes to the luminescent concentrator being easy to produce and easy to assemble and to no losses occurring within the luminescent concentrator on account of interfaces at different elements of the luminescent concentrator.

According to one development, the luminescent concentrator has a flat embodiment and comprises a first main side, a second main side lying opposite to the first main side, and at least one side face, which interconnects the first main side and the second main side. Preferably, the two main sides each have a flat embodiment and are embodied parallel to one another. Further, the side faces can each have a flat embodiment and/or can be embodied parallel to one another in pairwise fashion.

According to one development, the first main side comprises the entry face and the side face comprises the exit face. Since the first main side is relatively large in comparison with the side face, arranging the entry face on the first main side facilitates a particularly large entry face which is suitable for collecting a particularly large amount of light.

According to one development, the first main side comprises the entry face and the second main side comprises the exit face. The arrangement of the exit face on the second main side opposite to the first main side with the entry face is very advantageous since the light detector is then able to be assembled flat in a particularly simple manner.

According to one development, the first main side, the second main side, and/or the side face have an optically smooth embodiment. This contributes to a particularly large proportion of the light entering the luminescent concentrator by way of the entry face emerging from the exit face of the luminescent concentrator toward the light-sensitive area of the light detector following the conversion. The outer face being optically smooth means that a roughness depth of the outer face is small in comparison with the wavelength of the converted light.

According to one development, the side face has a form that is reflective for the modulated converted light. This contributes to relatively little modulated converted light emerging from the luminescent concentrator outside the exit face and hence contributes to a particularly high proportion of the modulated converted light emerging from the exit face and being detected by the light detector. If the exit face is formed on the second main side, all side faces can be formed reflective all around.

According to one development, the light detector is in optical contact with the luminescent concentrator. By way of example, the light detector is fastened to the luminescent concentrator by means of an adhesive, wherein the adhesive is transparent to the modulated converted light and has a refractive index that, for the converted light, is equal to or greater than the refractive index of the material of the luminescent concentrator. As a result, losses in the transition from the luminescent concentrator to the light detector are particularly low.

According to one development, the optical concentrator comprises a plastic with molecules suitable for photoluminescence and/or a monocrystalline inorganic phosphor body. This can contribute to the radiance or the luminance of the modulated converted light being particularly high.

According to one development, the entry face is more than four times larger, more than 10 times larger, more than 50 times larger or more than 100 times larger than the exit face and/or than a light-sensitive area of the light detector. This contributes to a particularly large amount of the modulated scattered light being able to be collected by means of the luminescent concentrator.

According to one development, a thickness of the luminescent concentrator, as measured from the first main side to the second main side, corresponds to 2% to 40% or 3% to 30% of a diameter or a diagonal of the first main side. This contributes to the luminescent concentrator and hence the heart rate monitor having a particularly thin embodiment.

According to one development, the luminescent concentrator has a ring-shaped embodiment and the light source is arranged in the interior of the corresponding ring shape. This contributes to a particularly high proportion of the modulated scattered light being able to be collected by the luminescent concentrator.

According to one development, the luminescent concentrator has a strip-shaped embodiment and comprises at least one second light source, the luminescent concentrator being arranged between the two light sources. This contributes to a particularly high proportion of the modulated scattered light being able to be collected by the luminescent concentrator.

According to one development, the luminescent concentrator has a disk-shaped embodiment and comprises at least one second light source, the light sources being arranged radially outside of the corresponding disk. This contributes to a particularly high proportion of the modulated scattered light being able to be collected by the luminescent concentrator.

According to one development, a thickness of the luminescent concentrator, as measured from the first main side to the second main side, lies in a range between 0.15 mm and 3 mm or between 0.2 mm and 2 mm, and/or the luminescent concentrator has a length of between 1.5 mm and 30 mm or between 2 mm and 20 mm on its longest side.

BRIEF DESCRIPTION OF THE DRAWINGS

Exemplary embodiments of the invention are illustrated in the figures and are explained in greater detail below.

In the following detailed description, reference is made to the accompanying drawings, which form part of this description and show for illustration purposes specific exemplary embodiments in which the invention can be implemented. Since component pails of exemplary embodiments can be positioned in a number of different orientations, the direction terminology serves for illustration and is not restrictive in any way whatsoever. It goes without saying that other exemplary embodiments can be used and structural or logical changes can be made, without departing from the scope of protection of the present invention. It goes without saying that the features of the various exemplary embodiments described herein can be combined with one another, unless specifically indicated otherwise. Therefore, the following detailed description should not be interpreted in a restrictive sense, and the scope of protection of the present invention is defined by the appended claims. In the figures, identical or similar elements are provided with identical reference signs, insofar as this is expedient.

DETAILED DESCRIPTION OF ILLUSTRATIVE EMBODIMENTS

FIG. 1 shows a lateral sectional illustration of a conventional pulse sensor 10 on a tissue 30 of a living being. The conventional pulse sensor 10 comprises at least one light source 22, two light sources in the exemplary embodiment shown, and a light detector 24. The light sources 22 and the light detector 24 are arranged in a housing of the conventional pulse sensor 10. The housing of the conventional pulse sensor 10 comprises two separating walls 26, which divide the interior of the housing into three chambers. The chambers can also be referred to as cavities. The light detector 24 is arranged in the central chamber and the light sources 22 are arranged in the outer chambers. The separating walls 26 serve to prevent light produced by means of the light sources 22 from directly reaching the light detector 24 without striking the tissue 30 beforehand.

The tissue 30 has a blood vessel 32 which extends through the tissue 30. By way of example, the blood vessel 32 can be a vein, a vessel, or an artery. The heart of the living being pumps blood through the blood vessel 32 in pulse-like fashion. As a result, the volume of the blood in the blood vessel 32 varies in corresponding pulse-like fashion. This leads to a pulse-like compression of the tissue 30 in the vicinity of the blood vessel 32.

By way of example, the light produced by means of the light sources 22 propagates along a first light path 40. The light propagating along the first light path 40 strikes the blood vessel 32 and is scattered by the blood vessel 32. During scattering, the light experiences a modulation that corresponds to the pulse of the living being. The light scattered by the blood vessel 32 consequently has a modulation, on the basis of which it is possible to draw conclusions about the pulse of the living being.

The light need not necessarily be scattered by the blood vessel 32 itself so that the scattered light has the modulation that corresponds to the pulse of the living being. The light can also be scattered within the blood vessel or in the vicinity of the blood vessel 32 and equally has the modulation corresponding to the pulse of the living being.

By way of example, the modulated scattered light can propagate along a second light path 42. The modulated scattered light propagating along the second light path 42 strikes a light-sensitive area of the light detector 24. The light detector 24 detects the modulated scattered light incident thereon and produces an output signal which is representative for the modulation and hence representative for the pulse of the living being. The output signal is transmitted to a controller (not shown), which establishes the pulse of the living being on the basis of the output signal. The controller can be arranged within the conventional pulse sensor 10 or outside of the conventional pulse sensor 10.

However, the modulated scattered light can also propagate along a third light path 44. The modulated scattered light propagating along the third light path 44 strikes one of the separating walls 26 and is absorbed by the latter or scattered in such a way that it can no longer be detected. This portion of the modulated scattered light is consequently not detected by the light detector 24.

Figure 2:
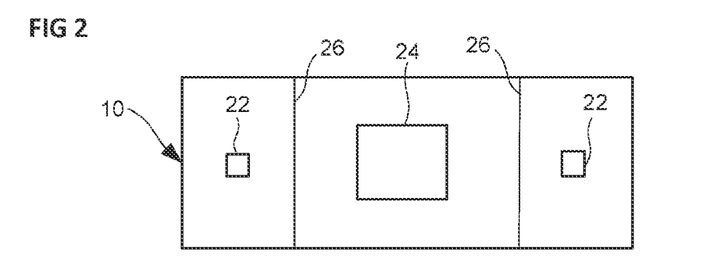
FIG. 2 shows a view from below of the conventional pulse sensor as per FIG. 1.

FIG. 2 shows a view from below of the conventional pulse sensor as per FIG. 1. It is evident from FIG. 2 that the light sources 22 and the light detector 24 are each arranged in separate chambers of the conventional pulse sensor 10 and that the chambers are open at the bottom such that the produced light can leave the conventional pulse sensor 10 in the direction of the tissue 30 and that the scattered light can reach the light detector 24.

Figure 3:
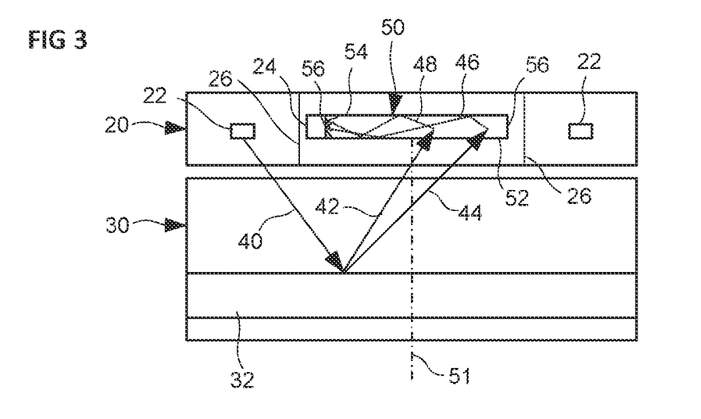
FIG. 3 shows a lateral sectional illustration of an exemplary embodiment of a pulse sensor on a tissue of a living being.

FIG. 3 shows a lateral sectional illustration of an exemplary embodiment of a pulse sensor 20 on a tissue 30 of a living being. The tissue 30 has the blood vessel 32 and corresponds to the tissue 30 explained above. The pulse sensor 20 largely corresponds to the pulse sensor 20 explained above. By way of example, the pulse sensor 20 also comprises at least one light source 22, two light sources in the exemplary embodiment shown, and a light detector 24. Moreover, the light sources 22 and the light detector 24 are likewise arranged in chambers of a housing of the pulse sensor 20 and shadowed from one another by the separating walls 26. The chambers in which the light sources 22 are arranged can be filled with a transparent material, for example silicone.

The pulse sensor 20 additionally comprises a luminescent concentrator 50. The luminescent concentrator 50 has a flat embodiment and comprises a first main side 52, which faces the tissue 30, a second main side 54, which lies opposite to the first main side 52, and a side face 56, preferably a plurality of side faces 56, which connect the first main side 52 to the second main side 54. The first main side 52 comprises an entry face of the luminescent concentrator 50, which likewise faces the tissue 30. The luminescent concentrator 50 is arranged in such a way that a sufficiently large amount of the modulated scattered light enters therein through the entry face. In particular, the entry face of the luminescent concentrator 50 is arranged in the second light path 42 and in the third light path 44, along which the modulated scattered light propagates.

The luminescent concentrator 50 comprises a fluorescent material or is formed therefrom. By way of example, the luminescent concentrator 50 comprises a plastic with fluorescent molecules or a fluorescent monocrystalline body or is formed therefrom. The modulated scattered light which has entered the luminescent concentrator 50 excites the fluorescent molecules within the luminescent concentrator 50 and converts the modulated scattered light in this way. In this process, converted light arises, which has a modulation that corresponds to the modulation of the modulated scattered light and hence to the pulse of the living being.

The luminescent concentrator 50 comprises an exit face which faces the light detector 24. The entry face is larger than the exit face. In the exemplary embodiment shown in FIG. 3, the exit face is formed on one of the side faces 56. The light detector 24 is arranged on the same side face 56. The luminescent concentrator 50 is in optical contact with the light detector 24.

The modulated converted light is guided in the luminescent concentrator 50 to the exit face. There, the modulated converted light emerges in the direction of the light-sensitive area of the light detector 24 and is detected by the light detector 24. The light detector 24 produces an electric output signal that is representative for the detected light and its modulation and, in particular, is representative for the pulse of the living being. An evaluation unit (not illustrated) can receive and evaluate the output signal of the light detector 24. In particular, the evaluation unit can establish the pulse of the living being on the basis of the modulation of the light.

The luminescent concentrator 50 can be in direct or indirect physical contact with the light detector 24. By way of example, the luminescent concentrator 50 can be fastened to the light-sensitive area of the light detector 24 by means of an adhesive.

Since the modulated scattered light is converted and the modulated converted light is detected, the luminescent concentrator 50 has an active effect. On account of this active effect, a radiance or a luminance of the light to be detected can be increased by means of the luminescent concentrator 50. On account of the increased radiance or luminance, it is also possible to achieve a higher irradiance or illuminance on the light-sensitive area of the light detector than in the case without a luminescent concentrator. Here, radiance is understood to mean the radiant power per étendue. Analogously, luminance is understood here to be the luminous flux per étendue.

Figure 4:
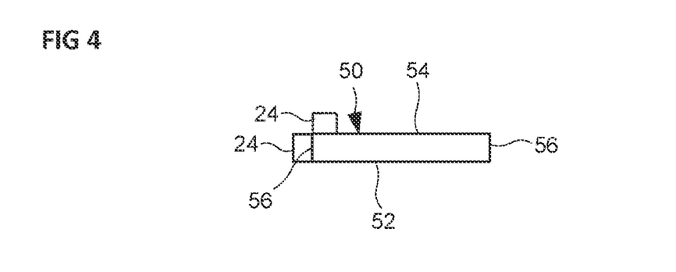
FIG. 4 shows a lateral sectional illustration of an exemplary embodiment of a luminescent concentrator and of a light detector.

FIG. 4 shows a lateral sectional illustration of an exemplary embodiment of a luminescent concentrator 50. By way of example, the luminescent concentrator 50 can correspond to the luminescent concentrator 50 explained with reference to FIG. 3. Optionally, the side faces 56 have a form that is reflective for the modulated converted light.

As an alternative or in addition to the light detector 24 arranged on one of the side faces 56 of the luminescent concentrator, a further light detector 24 can be arranged. In the exemplary embodiment shown in FIG. 4, the alternative or further light detector 24 is illustrated with the aid of dashed lines.

By way of example, the further light detector 24 is arranged on the second main side 54 of the luminescent concentrator 50. The further light detector 24 is in optical contact with the luminescent concentrator 50. As an alternative or in addition to the exit face, the luminescent concentrator 50 comprises a further exit face which is in optical contact with the further light detector 24. Accordingly, the further exit face is formed on the second main side 54 of the luminescent concentrator 50. In this case, the side faces 56 can have a form that is reflective for the modulated converted light.

Figure 5:
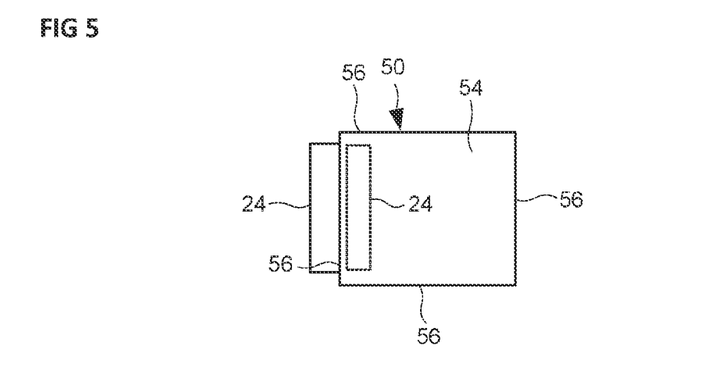
FIG. 5 shows a plan view of the luminescent concentrator and the light detector as per FIG. 4.

FIG. 5 shows a plan view of the luminescent concentrator as per FIG. 4.

Figure 6:
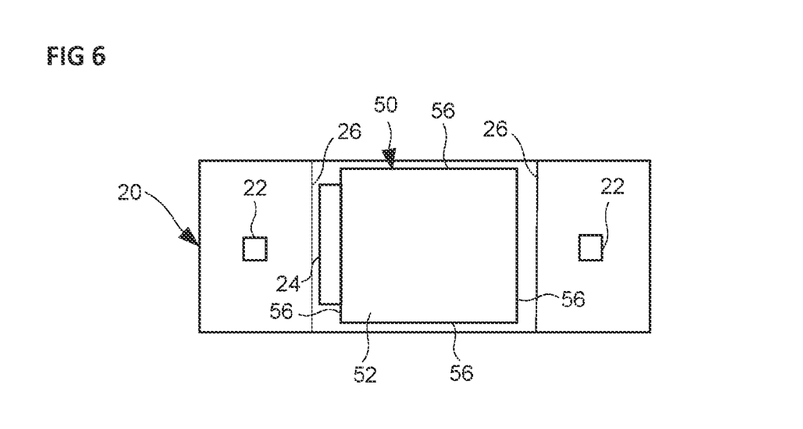
FIG. 6 shows a view from below of the exemplary embodiment of the pulse sensor as per FIG. 3.

FIG. 6 shows a view from below of the exemplary embodiment of the pulse sensor as per FIG. 3. It is evident from FIG. 6 that the light sources 22 and the light detector 24 are each arranged in separate chambers of the pulse sensor 20 and that the chambers are open at the bottom such that the produced light can leave the pulse sensor 20 in the direction of the tissue 30 and that the scattered light can reach the light detector 24.

A plurality of exemplary embodiments of the pulse sensor 2015 described below on the basis of schematic diagrams. The corresponding pulse sensors 20 substantially correspond to the pulse sensor 20 explained with reference to FIGS. 3 and 6, there only being a variation in the number and the arrangement of the light sources 22 and the light detectors 24 and in the form of the luminescent concentrator 50. To have a simpler illustration, the housing and the separating walls 26 are not illustrated in the following schematic diagrams.

Figure 7:
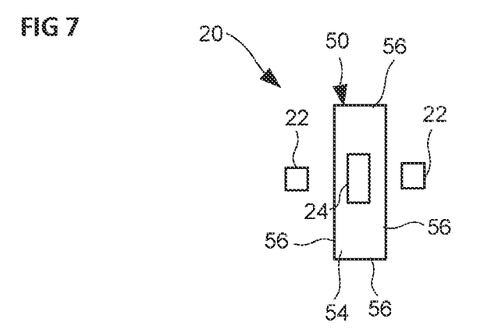
FIG. 7 shows a schematic diagram of an exemplary embodiment of a pulse sensor in a plan view.

FIG. 7 shows a schematic diagram of an exemplary embodiment of a pulse sensor 20 in a plan view. The luminescent concentrator 50 has a rectangular strip-shaped embodiment and extends perpendicular to a connecting line between two light sources 22. The light detector 24 is arranged centrally on the second main side 54 of the luminescent concentrator 50. The exit face of the luminescent concentrator 50 is arranged on the second main side 54 in such a way that it is in optical contact with the light-sensitive area of the light detector 24.

Figure 8:
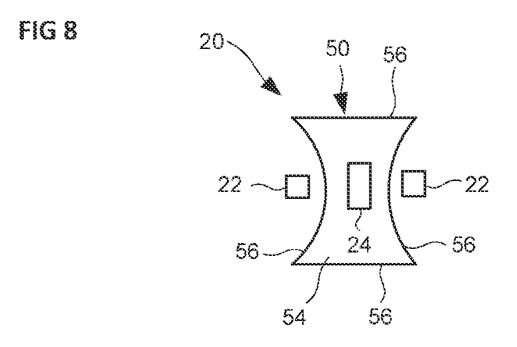
FIG. 8 shows a schematic diagram of an exemplary embodiment of a pulse sensor in a plan view.

FIG. 8 shows a schematic diagram of an exemplary embodiment of a pulse sensor 20 in a plan view. The luminescent concentrator 50 has a quadrangular strip-shaped embodiment, extends perpendicular to a connecting line between two light sources 22 and its side faces 56 facing the light sources 22 have such a concave embodiment that the corresponding side faces 56 extend at least partially around the light sources 22. The light detector 24 is arranged centrally on the second main side 54 of the luminescent concentrator 50. The exit face of the luminescent concentrator 50 is arranged on the second main side 54 in such a way that it is in optical contact with the light-sensitive area of the light detector 24.

Figure 9:
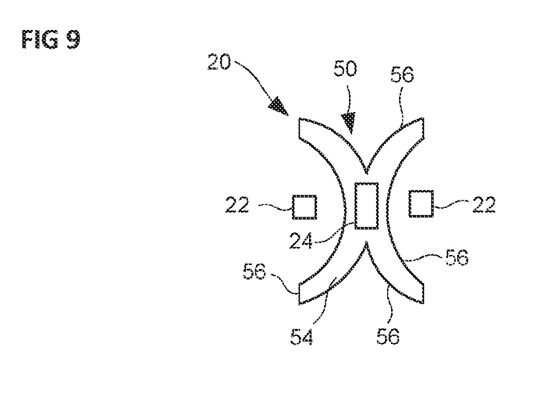
FIG. 9 shows a schematic diagram of an exemplary embodiment of a pulse sensor in a plan view.

FIG. 9 shows a schematic diagram of an exemplary embodiment of a pulse sensor 20 in a plan view. The luminescent concentrator 50 has the shape of two ring segments which merge into one another on their outer sides. The light detector 24 is arranged on the second main side 54 in the region in which the ring segments merge into one another. The exit face of the luminescent concentrator 50 is arranged on the second main side 54 in such a way that it is in optical contact with the light-sensitive area of the light detector 24.

Figure 10:
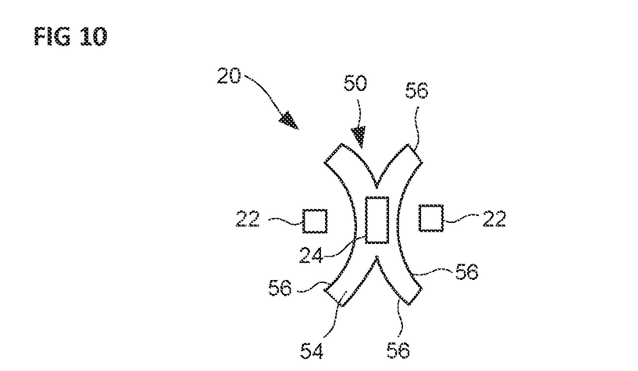
FIG. 10 shows a schematic diagram of an exemplary embodiment of a pulse sensor in a plan view.

FIG. 10 shows a schematic diagram of an exemplary embodiment of a pulse sensor 20 in a plan view. The luminescent concentrator 50 of this pulse sensor 20 substantially corresponds to the luminescent concentrator 50 explained with reference to FIG. 9, with the ends of the ring segments having a different shape to the luminescent concentrator 50 explained with reference to FIG. 9. The light detector 24 is arranged on the second main side 54 in the region in which the ring segments merge into one another. The exit face of the luminescent concentrator 50 is arranged on the second main side 54 in such a way that it is in optical contact with the light-sensitive area of the light detector 24.

Figure 11:
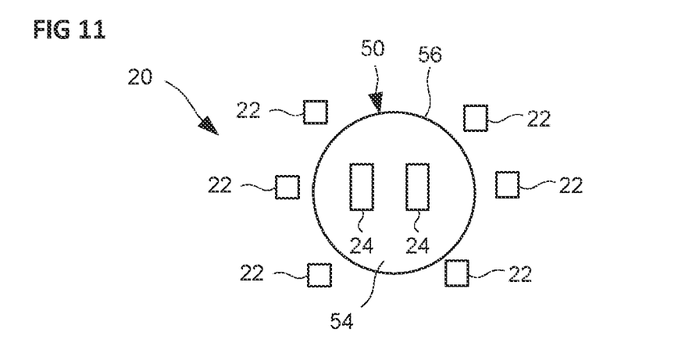
FIG. 11 shows a schematic diagram of an exemplary embodiment of a pulse sensor in a plan view.

FIG. 11 shows a schematic diagram of an exemplary embodiment of a pulse sensor 20 in a plan view. The luminescent concentrator 50 has a disk-shaped embodiment. Six light sources 22 are arranged radially outside of the luminescent concentrator 50. Two light detector 24 are arranged on the second main side 54 of the luminescent concentrator 50. The luminescent concentrator 50 has two exit faces on its second main side 54, said exit faces being arranged in such a way that they are each in optical contact with one of the light detectors 24.

Figure 12:
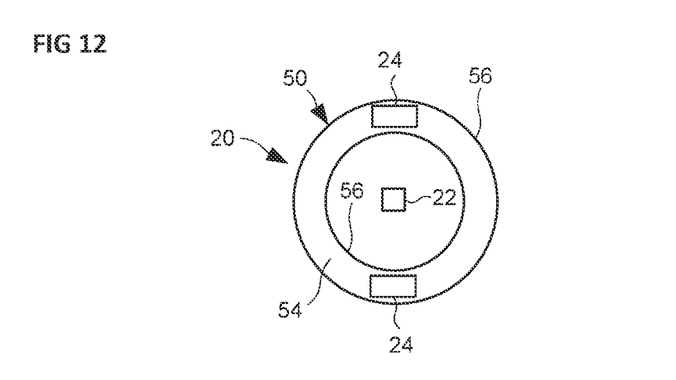
FIG. 12 shows a schematic diagram of an exemplary embodiment of a pulse sensor in a plan view.

FIG. 12 shows a schematic diagram of an exemplary embodiment of a pulse sensor 50 in a plan view. The luminescent concentrator 50 has a ring-shaped embodiment. The light source 22 is situated in the interior of the ring shape. Two light detectors 24 are arranged on the second main side 54. The luminescent concentrator 50 has two exit faces on its second main side 54, said exit faces being arranged in such a way that they are each in optical contact with one of the light detectors 24.

The invention is not restricted to the exemplary embodiments indicated. By way of example, the exemplary embodiments explained above can be combined with one another. By way of example, all of the exemplary embodiments shown can comprise only one light source 22 or more than two light sources 22. Further, all exemplary embodiments shown can comprise two or more light detectors 24. Further, all of the exemplary embodiments shown can comprise two or more luminescent concentrators 50. Further, each of the explained pulse sensors 20 can comprise a controller for driving the light sources 22 and/or for evaluating the output signal of the light detector 24. As an alternative thereto, the controller can be arranged outside of the pulse sensor 20.

The invention claimed is:

1. A pulse sensor comprising:
   two light sources configured to emit light in a direction of a perfused tissue of a living being so that the perfused tissue scatters the light and so that the scattered light is modulated on basis of a pulse of the living being;
   at least one luminescent concentrator comprising an entry face, an exit face smaller than the entry face, and a fluorescent material arranged in a light path between the entry face and the exit face,
   wherein the luminescent concentrator is configured to:
   receive at least some of the modulated scattered light entering through the entry face,
   convert the entered light by the fluorescent material, the converted light being modulated in a manner corresponding to the modulated scattered light, and
   emit the modulated converted light from the exit face; and
   one light detector configured to detect at least some of the modulated converted light emerging from the exit face,
   wherein, in plan view, the luminescent concentrator is strip-shaped and extends perpendicular to a connecting line between the two light sources,
   wherein side faces of the luminescent concentrator facing the light sources are concave, and
   wherein corresponding side faces extend at least partially around the light sources.

2. The pulse sensor as claimed in claim 1, wherein the luminescent concentrator is formed in one piece.

3. The pulse sensor as claimed in claim 1, wherein the luminescent concentrator is flat and comprises a first main side, a second main side arranged opposite to the first main side, and at least one side face connecting the first main side and the second main side.

4. The pulse sensor as claimed in claim 3, wherein the light detector is arranged centrally on the second main side of the luminescent concentrator and the exit face of the luminescent concentrator is arranged on the second main side such that it is in optical contact with a light-sensitive area of the light detector.

5. The pulse sensor as claimed in claim 3, wherein the luminescent concentrator is quadrangular strip-shaped.

6. The pulse sensor as claimed in claim 3, wherein the first main side, the second main side, and/or the side face is optically smooth.

7. The pulse sensor as claimed in claim 3, wherein the side face is reflective for the modulated converted light.

8. The pulse sensor as claimed in claim 3, wherein the entry face is more than four times larger than the exit face and/or than a light-sensitive area of the light detector.

9. The pulse sensor as claimed in claim 3,
   wherein a thickness of the luminescent concentrator, as measured from the first main side to the second main side, is in a range of between 0.15 mm and 3 mm, inclusive, and/or
   wherein the luminescent concentrator has a length of between 1.5 mm and 30 mm, inclusive, in every direction.

10. The pulse sensor as claimed in claim 1, wherein the luminescent concentrator comprises a plastic with molecules suitable for photoluminescence and/or a monocrystalline inorganic phosphor body.

11. A pulse sensor comprising:
    two light sources configured to emit light in a direction of a perfused tissue of a living being so that the perfused tissue scatters the light and so that the scattered light is modulated on basis of a pulse of the living being;

at least one luminescent concentrator comprising an entry face, an exit face smaller than the entry face, and a fluorescent material arranged in a light path between the entry face and the exit face, wherein the luminescent concentrator is configured to:

receive at least some of the modulated scattered light entering through the entry face, convert the entered light by the fluorescent material, the converted light being modulated in a manner corresponding to the modulated scattered light, and emit the modulated converted light from the exit face; and one light detector configured to detect at least some of the modulated converted light emerging from the exit face, wherein, in a plan view, the luminescent concentrator is strip-shaped and extends perpendicular to a connecting line between the two light sources and its side faces facing the light sources have a concave embodiment and wherein corresponding side faces extend at least partially around the light sources, wherein the luminescent concentrator is flat and comprises a first main side, a second main side located opposite to the first main side, and at least one side face connecting the first main side and the second main side, wherein the light detector is arranged centrally on the second main side of the luminescent concentrator and the exit face of the luminescent concentrator is arranged on the second main side such that it is in optical contact with a light-sensitive area of the light detector.

12. The pulse sensor as claimed in claim 11, wherein the luminescent concentrator is quadrangular strip-shaped.

13. The pulse sensor as claimed in claim 11, wherein the entry face is more than four times larger than the exit face and/or than the light-sensitive area of the light detector.

14. A pulse sensor comprising:

two light sources configured to emit light in a direction of a perfused tissue of a living being so that the perfused tissue scatters the light and so that the scattered light is modulated on basis of a pulse of the living being;

at least one luminescent concentrator comprising an entry face, an exit face smaller than the entry face, and a fluorescent material arranged in a light path between the entry face and the exit face, wherein the luminescent concentrator is configured to:

receive at least some of the modulated scattered light entering through the entry face, convert the entered light by the fluorescent material, the converted light being modulated in a manner corresponding to the modulated scattered light, and emit the modulated converted light from the exit face; and one light detector configured to detect at least some of the modulated converted light emerging from the exit face, wherein the luminescent concentrator is flat and comprises a first main side, a second main side located opposite to the first main side, and at least one side face connecting the first main side and the second main side, wherein the luminescent concentrator comprises two ring segments which merge into one another on their outer sides and the light detector is arranged on the second main side in a region in which the ring segments merge into one another, and wherein the exit face of the luminescent concentrator is arranged on the second main side such that it is in optical contact with a light-sensitive area of the light detector.

15. The pulse sensor as claimed in claim 14, wherein the luminescent concentrator is formed in one piece.

16. The pulse sensor as claimed in claim 14, wherein the first main side, the second main side, and/or the side face are optically smooth.

17. The pulse sensor as claimed in claim 14, wherein the side face is reflective for the modulated converted light.

18. The pulse sensor as claimed in claim 14, wherein the luminescent concentrator comprises a plastic with molecules suitable for photoluminescence and/or a monocrystalline inorganic phosphor body.

19. The pulse sensor as claimed in claim 14, wherein the entry face is more than four times larger than the exit face and/or than the light-sensitive area of the light detector.

20. The pulse sensor as claimed in claim 14, wherein a thickness of the luminescent concentrator, as measured from the first main side to the second main side, is in a range of between 0.15 mm and 3 mm, inclusive, and/or wherein the luminescent concentrator has a length of between 1.5 mm and 30 mm, inclusive, in every direction.

* * * * *